(12) United States Patent
Kolczewski et al.

(10) Patent No.: US 8,350,028 B2
(45) Date of Patent: Jan. 8, 2013

(54) 2-AMINOQUINOLINES

(75) Inventors: Sabine Kolczewski, Loerrach (DE); Claus Riemer, Freiburg (DE); Olivier Roche, Folgensbourg (FR); Lucinda Steward, Basel (CH); Juergen Wichmann, Steinen (DE); Thomas Woltering, Freiburg (DE)

(73) Assignee: Hofmann-La Roche Inc., Nutley, NJ (US)

( * ) Notice: Subject to any disclaimer, the term of this patent is extended or adjusted under 35 U.S.C. 154(b) by 709 days.

(21) Appl. No.: 12/398,415

(22) Filed: Mar. 5, 2009

(65) Prior Publication Data
US 2009/0233927 A1 Sep. 17, 2009

(30) Foreign Application Priority Data
Mar. 12, 2008 (EP) .................................... 08152618

(51) Int. Cl.
*C07D 215/38* (2006.01)
*C07D 413/02* (2006.01)

(52) U.S. Cl. ........................ 544/128; 546/159

(58) Field of Classification Search ........................ None
See application file for complete search history.

(56) References Cited

U.S. PATENT DOCUMENTS
2007/0299074 A1 12/2007 Netz et al.

FOREIGN PATENT DOCUMENTS

| WO | WO 03/045313 | 6/2003 |
|---|---|---|
| WO | WO 2004/080463 | 9/2004 |
| WO | WO 2004/096771 | 11/2004 |
| WO | WO 2005/082871 | 9/2005 |
| WO | WO 2007/022946 | 3/2007 |

OTHER PUBLICATIONS

Hoyer et al., Pharmacol. Rev. vol. 46, pp. 157-204 (1994).
Rees et al., FEBS Lett. vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Thomas, D. R., Pharmacol. Ther. vol. 111(3) pp. 707-714 (2006).
Doly et al., The Journal of Comparative Neurology vol. 476 pp. 316-329 (2004).
Dubertret et al., J. of Psychiatric Research vol. 35 pp. 371-376 (2004).
Garcia-Ladona et al., 36th Annual Meeting Soc. Neurosci. 10/14-10/18, Atlanta Abstract 33.1 (2006).
Drescher et al., 36th Annual Meeting Soc. Neurosci. 10/14-10/18, Atlanta Abstract 33.2 (2006).
Thomas, Neuropharmacology vol. 51(3) pp. 566-577 (2006).
Barnes et al., Neuropharmacology vol. 38 pp. 1083-1152 (1999).
Pasqualetti et al., Mol. Brain Res. vol. 56 pp. 1-8 (1998).
Wang et al., Neurosci. Lett. vol. 278 pp. 9-12 (2000).
Birkett et al., Neuroreport vol. 11 pp. 2017-2020 (2000).
Iwata et al., Mol. Psychiatry vol. 6 pp. 217-219 (2001).
Duncan et al., Brain Research vol. 869, pp. 178-185 (2000).
Sprouse et al., Synapse, vol. 54(2) pp. 111-118 (2004).
Bennett et al., "Journal of the Chemical Society":227-232 ( 1949).

*Primary Examiner* — Janet Andres
*Assistant Examiner* — Timothy R Rozof
(74) *Attorney, Agent, or Firm* — George W. Johnston; Patricia S. Rocha-Tramaloni; Kimberly J. Prior

(57) ABSTRACT

The present invention is concerned with 2-aminoquinoline derivatives of formula I

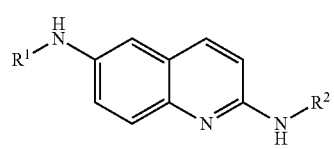

wherein $R^1$ and $R^2$ are as described herein and pharmaceutically acceptable salts thereof, pharmaceutical compositions containing them, and methods for their manufacture. These compounds are $5\text{-HT}_{5A}$ receptor antagonists, useful for the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders such as Parkinson's disease, psychiatric disorders or gastrointestinal disorders.

14 Claims, No Drawings

2-AMINOQUINOLINES

PRIORITY OF RELATED APPLICATION(S)

This application claims the benefit of European Patent Application No. 08152618.8, filed Mar. 12, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-$HT_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-$HT_{5A}$ serotonin receptor has been described in *FEBS Letters*, 355, 242-246 (1994). The sequence is not closely related to that of any previously known serotonin receptor, with the best homology being 35% to the human 5-$HT_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-$HT_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of 5-$HT_{5A}$ receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the 5-$HT_{5A}$ receptor in the rat spinal cord that 5-$HT_{5A}$ receptors may play a role in central motor control, nociception and autonomic function such as stress induced urinary incontinence and overactive bladder. The *Journal of Psychiatric Research*, 38, 371-376 (2004) describes evidence for a potential significant role of the 5-$HT_{5A}$ gene in schizophrenia and more specifically in patients with later age at onset.

SUMMARY OF THE INVENTION

The present invention provides 2-aminoquinoline derivatives. In particular, the present invention provides compounds of formula (I)

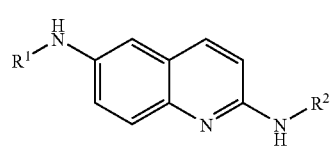

wherein
$R^1$ is —C(O)-cycloalkyl, —C(O)-alkyl, —C(O)-alkylene-cycloalkyl, —C(O)-alkylene-heterocycloalkyl, —C(O)-heterocycloalkyl, —C(O)—$NR^aR^b$, —$S(O)_2$-heterocycloalkyl, —$S(O)_2$—$NR^cR^d$, alkyl, haloalkyl, cyanoalkyl, hydroxyalkyl, -alkylene-cycloalkyl, -alkylene-heterocycloalkyl, -alkylene-$NR^eR^f$, -alkylene-O-alkyl, or -alkylene-$S(O)_x$-alkyl;
x is 0, 1 or 2;
$R^a$, $R^b$, $R^c$, $R^d$, $R^e$, and $R^f$ are each independently selected from H, alkyl, cycloalkyl, and heterocycloalkyl;
heterocycloalkyl is unsubstituted or substituted with one or more substituents independently selected from alkyl, hydroxy, hydroxyalkyl, benzyl, oxo, —C(O)Oalkyl, cycloalkyl, alkylene-O-alkyl, —C(O)haloalkyl, —C(O)alkylene-O-alkyl, cyanoalkyl, alkylene-$S(O)_x$-alkyl, -alkylene-C(O)N(alkyl)$_2$, halo, haloalkyl and alkoxy;
$R^2$ is —$Ar^1$, —$CH_2$—$Ar^1$, or —$CH_2CH_2O$—$Ar^1$;
$Ar^1$ is phenyl or 5- or 6-membered heteroaryl, each unsubstituted or substituted with one or more alkyl, cycloalkyl, alkoxy, haloalkoxy, haloalkyl, halo, OH, or CN, or with two substituents in the ortho-position that form a bridge anellated to the aromatic ring, wherein the bridge is selected from —O—$CH_2CH_2O$—, —$OCHCH_3CH_2$—, or —$OC(CH_3)_2CH_2$—, and wherein phenyl is not substituted with halo in para-position.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof.

The present invention also provides pharmaceutical compositions containing a therapeutically effective amount of a compound of formula I or a pharmaceutically acceptable salt thereof and a pharmaceutically acceptable carrier. The invention further provides methods for the manufacture of the compounds and compositions of the invention.

Compounds of formula I have good activity on the 5-$HT_{5A}$ receptor. Therefore, the invention provides compounds of formula I or pharmaceutically acceptable salts thereof as well as their use in the manufacture of medicaments for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "allyl" denotes a group —$CH_2CH$=$CH_2$.

As used herein, the term "alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms.

As used herein, the term "alkylene" means a linear saturated divalent hydrocarbon radical of one to seven carbon atoms or a branched saturated divalent hydrocarbon radical of three to seven carbon atoms. Preferred are divalent hydrocarbon radicals of one to four carbon atoms. In case alkylene is located in between two heteroatoms, it is preferably from 2 to 7 carbon atoms, more preferably from 2 to 4 carbon atoms.

The term "halo" denotes chloro, iodo, fluoro and bromo. Preferred halo are fluoro, chloro and bromo, more preferred are fluoro and chloro.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. Preferably 2-fluoroethyl, 2,2,2-trifluoroethyl, fluoromethyl, or trifluoromethyl.

The term "hydroxyalkyl" denotes an alkyl group as defined above wherein at least one of the hydrogen atoms of the alkyl group is replaced by a hydroxy group. Examples of hydroxyalkyl include but are not limited to methyl, ethyl, propyl, isopropyl, isobutyl, sec-butyl, tert-butyl, pentyl or n-hexyl substituted by one or more OH, as well as those groups specifically illustrated by the examples herein below.

The term "cyanoalkyl" denotes an alkyl group as defined above wherein at least one of the hydrogen atoms of the alkyl group is replaced by a cyano group. Examples of cyanoalkyl include but are not limited to methyl, ethyl, propyl, isopropyl, isobutyl, sec-butyl, tert-butyl, pentyl or n-hexyl substituted by one or more CN, as well as those groups specifically illustrated by the examples herein below.

The term "alkoxy" denotes a group —O—R' wherein R' is alkyl as defined above.

The term "aromatic" means the presence of an electron sextet in a ring, according to Hückel's rule.

The term "cycloalkyl" refers to a monovalent saturated monocyclic or bicyclic hydrocarbon radical of 3 to 8 ring carbon atoms. Bicyclic means consisting of two saturated carbocycles having two carbon atoms in common, i.e. the bridge separating the two rings is either a single bond or a chain of preferably one or two carbon atoms. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, and bicyclo[2.2.2]octanyl. Preferred cycloalkyl is a monocyclic hydrocarbon radical of 3 to 6 ring carbon atoms, and preferred examples are cyclopropyl, cyclopentyl and cyclohexyl.

The term "heterocycloalkyl" refers to a monovalent saturated 5- to 9-membered monocyclic or bicyclic ring system containing one, two or three ring heteroatoms selected from N, O and S, the remaining ring atoms being carbon atoms. In case of monocyclic heterocycloalkyl, the ring is preferably 5- or 6-membered, in case of bicyclic heterocycloalkyl, the bicyclic ring is preferably 7-, 8- or 9-membered. "Heterocycloalkyl" is unsubstituted or substituted as described herein. Examples for substituents on heterocycloalkyl are independently selected from alkyl, hydroxy, hydroxyalkyl, benzyl, oxo, —C(O)Oalkyl, cycloalkyl, alkylene-O-alkyl, —C(O) haloalkyl, —C(O)-alkylene-O-alkyl, cyanoalkyl, alkylene-S(O)$_x$-alkyl, -alkylene-C(O)N(alkyl)$_2$, halo, haloalkyl and alkoxy, wherein x is 0, 1, or 2.

The term "5- or 6-membered heterocycloalkyl" refers to a monovalent saturated monocycle as defined above. Preferably, 5- or 6-membered heterocycloalkyl is a monovalent saturated monocyclic ring containing one or two ring heteroatoms selected from N, O, and S. Examples for 5- or 6-membered heterocycloalkyl moieties are tetrahydropyranyl, tetrahydrothiopyranyl, tetrahydrofuranyl, tetrahydrothiophenyl, pyrrolidinyl, imidazolidinyl, morpholinyl, thiomorpholinyl, piperidinyl, and piperazinyl. Preferred examples are morpholinyl, piperidinyl and piperazinyl. The 5- or 6-membered heterocycloalkyl moiety is optionally substituted as described herein.

The term "7-, 8- or 9-membered bicyclic heterocycloalkyl" refers to a saturated bicyclic ring system as defined above. Preferably, 7-, 8- or 9-membered bicyclic heterocycloalkyl is a monovalent saturated bicyclic ring system containing one or two ring heteroatoms selected from N, O and S. Thereby, "bicyclic" describes a system consisting of two saturated rings having two ring atoms in common, i.e. the bridge separating the two rings is either a bond or a chain of preferably one or two atoms. Examples for 7-, 8- or 9-membered bicyclic heterocycloalkyl are 2-oxa-5-aza-hicyclo[2.2.1]heptyl, 8-oxa-3-aza-bicyclo[3.2.1]octyl, 8-aza-bicyclo[3.2.1]octyl, 3-oxa-9-aza-bicyclo[3.3.1]nonyl, 9-aza-bicyclo[3.3.1]nonyl and 3-thia-9-aza-bicyclo[3.3.1]nonyl. A preferred example for bicyclic heterocycloalkyl is 2-oxa-5-aza-hicyclo[2.2.1]heptyl, in particular (1S,4S)-2-oxa-5-aza-hicyclo[2.2.1]heptyl. 7-, 8- or 9-membered bicyclic heterocycloalkyl is optionally substituted as described herein.

The term "heteroaryl" as defined herein denotes a monovalent monocyclic or bicyclic aromatic ring system of 5 or 6 ring atoms containing one, two, or three ring heteroatoms selected from N, O, and S, the remaining ring atoms being C. Examples of heteroaryl moieties include, but are not limited to thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl and pyridazinyl. A preferred example for heteroaryl is furanyl. The heteroaryl is optionally substituted as defined herein and are in principle the same as those for phenyl. Examples for substituents on heteroaryl include, but are not limited to alkyl, cycloalkyl, alkoxy, haloalkoxy, haloalkyl, halo, OH, or CN, or an anellated bridge selected from —O—CH$_2$CH$_2$O—, —O—CHCH$_3$CH$_2$—, and —O—C(CH$_3$)$_2$CH$_2$—. A preferred substituent on heteroaryl is alkyl.

Analogously to the heteroaryl system, phenyl can be unsubstituted or substituted with one or more substituents selected from alkyl, cycloalkyl, alkoxy, haloalkoxy, haloalkyl, halo, OH, and CN, or an anellated bridge selected from —O—CH$_2$CH$_2$O—, —O—CHCH$_3$CH$_2$—, and —O—C(CH$_3$)$_2$CH$_2$—, however, wherein phenyl is not para-substituted with halo. Preferred substituents on phenyl are alkoxy, or an anellated bridge selected from —O—CHCH$_3$CH$_2$— and —O—C(CH$_3$)$_2$CH$_2$—.

The term "thiophenyl" as used herein is synonymous with "thienyl" and denotes a thiophene substituent, i.e., C$_4$H$_4$S.

When indicating the number of substituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention provides compounds of formula (I)

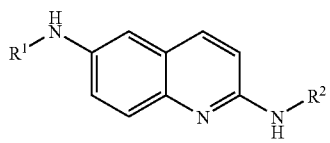

I wherein
R$^1$ is —C(O)-cycloalkyl, —C(O)alkyl, —C(O)-alkylene-cycloalkyl, —C(O)-alkylene-heterocycloalkyl, —C(O)-heterocycloalkyl, —C(O)—NR$^a$R$^b$, —S(O)$_2$-heterocycloalkyl, —S(O)$_2$—NR$^c$R$^d$, alkyl, haloalkyl, cyanoalkyl, hydroxyalkyl, -alkylene-cycloalkyl, -alkylene-heterocycloalkyl, -alkylene-NR$^e$R$^f$, -alkylene-O-alkyl, or -alkylene-S(O)$_x$-alkyl;
x is 0, 1 or 2;
R$^a$, R$^b$, R$^c$, R$^d$, R$^e$, and R$^f$ are each independently selected from H, alkyl, cycloalkyl, and heterocycloalkyl;
heterocycloalkyl is unsubstituted or substituted with one or more substituents independently selected from alkyl, hydroxy, hydroxyalkyl, benzyl, oxo, —C(O)Oalkyl, cycloalkyl, alkylene-O-alkyl, —C(O)haloalkyl, —C(O)-alkylene-O-alkyl, cyanoalkyl, alkylene-S(O)$_x$-alkyl, -alkylene-C(O)N(alkyl)$_2$, halo, haloalkyl and alkoxy;
R$^2$ is —Ar$^1$, —CH$_2$—Ar$^1$, or —CH$_2$CH$_2$O—Ar$^1$;
Ar$^1$ is phenyl or 5- or 6-membered heteroaryl, each unsubstituted or substituted with one or more alkyl, cycloalkyl, alkoxy, haloalkoxy, haloalkyl, halo, OH, or CN, or with two substituents in the ortho-position that form a bridge anellated to the aromatic ring, wherein the bridge is selected from —O—CH$_2$CH$_2$O—, —OCHCH$_3$CH$_2$—, and —OC(CH$_3$)$_2$CH$_2$—, and wherein phenyl is not substituted with halo in para-position;
or a pharmaceutically acceptable salt thereof.

In certain embodiments,
R$^1$ is —C(O)-cycloalkyl, —C(O)-alkylene-heterocycloalkyl, —C(O)-heterocycloalkyl, —C(O)—NR$^a$R$^b$, —S(O)$_2$-heterocycloalkyl, —S(O)$_2$—NR$^c$R$^d$, alkyl, -alkylene-cycloalkyl, -alkylene-heterocycloalkyl, -alkylene-NR$^e$R$^f$, or -alkylene-O-alkyl,
R$^a$, R$^b$, R$^c$, R$^d$, R$^e$, and R$^f$ are each independently selected from H, alkyl, cycloalkyl, and heterocycloalkyl; and
heterocycloalkyl is unsubstituted or substituted with one or more substituents independently selected from alkyl, hydroxy, hydroxyalkyl, benzyl, oxo, —C(O)Oalkyl, cycloalkyl, alkylene-O-alkyl, —C(O)haloalkyl, —C(O)-alkylene-O-alkyl, cyanoalkyl, alkylene-S(O)$_x$-alkyl, -alkylene-C(O)N(alkyl)$_2$, halo, haloalkyl and alkoxy, and
x is 0, 1 or 2.

In certain embodiments,
R$^1$ is —C(O)-cycloalkyl, —C(O)-alkylene-heterocycloalkyl, —C(O)-heterocycloalkyl, —C(O)—NR$^a$R$^b$, —S(O)$_2$-heterocycloalkyl, —S(O)$_2$—NR$^c$R$^d$, alkyl, -alkylene-cycloalkyl, -alkylene-heterocycloalkyl, -alkylene-NR$^e$R$^f$, or -alkylene-O-alkyl,
R$^a$, R$^b$, R$^c$, R$^d$, R$^e$, and R$^f$ are each independently selected from H, alkyl, cycloalkyl, and heterocycloalkyl; and
heterocycloalkyl is unsubstituted or substituted with one or more substituents independently selected from alkyl, —C(O)haloalkyl, —C(O)-alkylene-O-alkyl, alkylene-S(O)$_x$-alkyl, and haloalkyl; and x is 0, 1 or 2.

In certain embodiments,
R$^a$ and R$^b$ are each independently selected from H, alkyl, and heterocycloalkyl, wherein heterocycloalkyl is as defined herein.

In certain embodiments,
R$^c$ and R$^d$ are each independently selected from H, alkyl and cycloalkyl.

In certain embodiments,
R$^e$ and R$^f$ are alkyl.

In all embodiments, heterocycloalkyl is as defined above. Preferably, heterocycloalkyl is morpholinyl, piperidinyl, piperazinyl or 2-oxa-5-aza-hicyclo[2.2.1]heptyl, each unsubstituted or substituted with one or more substituents independently selected from alkyl, —C(O)haloalkyl, —C(O)-alkylene-O-alkyl, alkylene-S(O)$_x$-alkyl, and haloalkyl.

In certain embodiments,
R$^2$ is —Ar$^1$, —CH$_2$—Ar$^1$, or —CH$_2$CH$_2$O—Ar$^1$;
Ar$^1$ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—CH$_2$CH$_2$O—, —OCHCH$_3$CH$_2$—, and —OC(CH$_3$)$_2$CH$_2$—.

In certain embodiments,
R² is —Ar¹, wherein
Ar¹ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—CH₂CH₂O—, —OCHCH₃CH₂—, and —OC(CH₃)₂CH₂—.

In certain embodiments,
R² is —CH₂—Ar¹, wherein
Ar¹ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—CH₂CH₂O—, —OCHCH₃CH₂—, and —OC(CH₃)₂CH₂—.

In certain embodiments,
R² is —CH₂CH₂O—Ar¹; wherein
Ar¹ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—CH₂CH₂O—, —OCHCH₃CH₂—, and —OC(CH₃)₂CH₂—.

In certain embodiments,
R² is —Ar¹, —CH₂—Ar¹, or —CH₂CH₂O—Ar¹;
Ar¹ is phenyl or 5- or 6-membered heteroaryl, each unsubstituted or substituted with one or more alkyl or alkoxy, or with two substituents in the ortho-position and that form a bridge anellated to the aromatic ring, the bridge being selected from —OCHCH₃CH₂— and —OC(CH₃)₂CH₂—.

In all embodiments, heteroaryl is as defined above; unsubstituted or substituted as defined above.

In certain embodiments, heteroaryl is furanyl, unsubstituted or substituted as defined above.

In certain embodiments,
R² is —Ar¹, —CH₂—Ar¹, or —CH₂CH₂O—Ar¹; and
Ar¹ is phenyl, 4-methoxy-phenyl, 2-methoxy-phenyl, 2,4-dimethoxy-phenyl, 5-methyl-furan-2-yl, 2-methyl-2,3-dihydro-benzofuran-7-yl, or 2,2-dimethyl-2,3-dihydro-benzofuran-7-yl.

It is to be understood that all combinations of R¹ and R² as disclosed herein are encompassed by present invention.

Preferred compounds of formula I are those as shown in the examples below.

More preferred compounds of formula I are:
N'-{2-[(2-methoxybenzyl)amino]quinolin-6-yl}-N,N-dimethylsulfamide,
1-isopropyl-3-[2-(2-methoxy-benzylamino)-quinolin-6-yl]-urea,
1-[2-(2-methoxy-benzylamino)-quinolin-6-yl]-3-(1-methyl-piperidin-4-yl)-urea,
1-isopropyl-3-[2-(4-methoxy-benzylamino)-quinolin-6-yl]-urea,
(1S,4S)-2-oxa-5-aza-bicyclo[2.2.1]heptane-5-sulfonic acid [2-(2-methoxy-benzylamino)-quinolin-6-yl]-amide,
N-cyclopropyl-N'-{2-[(2-methoxybenzyl)amino]quinolin-6-yl}sulfamide,
1-isopropyl-3-{2-[(5-methyl-furan-2-ylmethyl)-amino]-quinolin-6-yl}-urea,
1-[2-(2-methoxy-benzylamino)-quinolin-6-yl]-3-[1-(2-methoxy-ethyl)-piperidin-4-yl]-urea,
1-[1-(2-fluoro-ethyl)-piperidin-4-yl]-3-[2-(2-methoxy-benzylamino)-quinolin-6-yl]-urea,
1-(1-isopropyl-piperidin-4-yl)-3-[2-(2-methoxy-benzylamino)-quinolin-6-yl]-urea,
1-[2-(2-methoxy-benzylamino)-quinolin-6-yl]-3-[1-(3,3,3-trifluoro-propionyl)-piperidin-4-yl]-urea,
1-[1-(2-fluoro-acetyl)-piperidin-4-yl]-3-[2-(2-methoxy-benzylamino)-quinolin-6-yl]-urea,
1-(1-cyclopropyl-piperidin-4-yl)-3-[2-(2-methoxy-benzylamino)-quinolin-6-yl]-urea,
1-{2-[(5-methyl-furan-2-ylmethyl)-amino]-quinolin-6-yl}-3-(1-methyl-piperidin-4-yl)-urea,
1-[2-(2-methoxy-benzylamino)-quinolin-6-yl]-3-[1-(2-methylsulfanyl-ethyl)-piperidin-4-yl]-urea,
1-[1-(2-methoxy-acetyl)-piperidin-4-yl]-3-[2-(2-methoxybenzylamino)-quinolin-6-yl]-urea,
cyclopropanecarboxylic acid [2-(2-methoxy-benzylamino)-quinolin-6-yl]-amide, and
N-[2-(2-methoxy-benzylamino)-quinolin-6-yl]-2-(4-methyl-piperazin-1-yl)-acetamide.

The present compounds of formula I, their starting materials, their pharmaceutically acceptable salts, and their optical isomers can be prepared by methods known in the art.

For example, a process to synthesize representative compounds of formula I

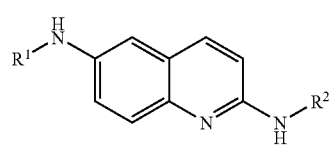

I can be used which comprises one of the following steps:
a) reacting a compound 2

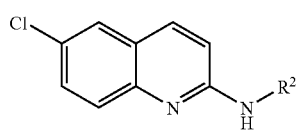

2 with an amine of formula R¹NH₂ wherein R¹ is alkyl, haloalkyl, cyanoalkyl, hydroxyalkyl, -alkylene-cycloalkyl, -alkylene-heterocycloalkyl, -alkylene-NRᵉRᶠ, -alkylene-O-alkyl, or -alkylene-S(O)ₓ-alkyl, to give a compound of formula I wherein R¹ is alkyl, haloalkyl, cyanoalkyl, hydroxyalkyl, -alkylene-cycloalkyl, -alkylene-heterocycloalkyl, -alkylene-NRᵉRᶠ, -alkylene-O-alkyl, or -alkylene-S(O)ₓ-alkyl;

b) reacting a compound 6

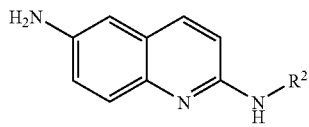

6 b1) with a compound of formula 6a

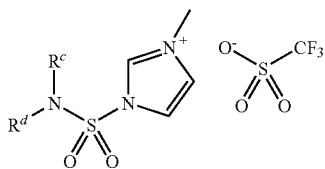

or alternatively,
b2) with a sulfamoyl chloride of formula 6b

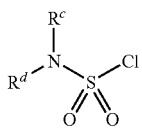

wherein $R^c$ and $R^d$ are each independently H, alkyl, cycloalkyl, or heterocycloalkyl, preferably from H, alkyl or cycloalkyl, to give a compound of formula I wherein $R^1$ is $-S(O)_2NR^cR^d$;
b3) with an isocyanate of formula 6c

wherein $R^a$ and $R^b$ are each independently H, alkyl, cycloalkyl, or heterocycloalkyl, to give a compound of formula I wherein $R^1$ is $-C(O)NR^aR^b$;
b4) with an amine of formula $R^BNH_2$,
wherein $R^B$ is alkyl, cycloalkyl, or heterocycloalkyl, to give a compound of formula I wherein $R^1$ is $-C(O)NR^aR^b$ with $R^a$ being H and $R^b$ being alkyl, cycloalkyl, or heterocycloalkyl;
b5) with a compound of formula $R^4C(O)LG$, wherein LG is Cl or $R^4C(O)LG$ is an activated ester formed in situ with a coupling agent, and $R^4$ is cycloalkyl, alkyl, alkylene-cycloalkyl, -alkylene-heterocycloalkyl, heterocycloalkyl, or $-NR^aR^b$, wherein $R^a$ and $R^b$ are each independently H, alkyl, cycloalkyl, or heterocycloalkyl; to give a compound of formula I wherein $R^1$ is $-C(O)$-cycloalkyl, $-C(O)$-alkyl, $-C(O)$-alkylene-cycloalkyl, $-C(O)$-alkylene-heterocycloalkyl, $-C(O)$-heterocycloalkyl, or $-C(O)-NR^aR^b$, wherein $R^a$ and $R^b$ are each independently H, alkyl, cycloalkyl, or heterocycloalkyl.

As mentioned earlier, the compounds of formula I and their pharmaceutically acceptable addition salts possess valuable pharmaceutical properties. Compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and Ki values calculated using the Cheng-Prussoff equation.

The activity of the compounds according to the invention is exemplified in the table 1 below:

| Ex. No. | Ki (nM) |
| --- | --- |
| 10 | 17.1 |
| 14 | 3.3 |
| 17 | 2.7 |
| 18 | 49.5 |
| 19 | 8.0 |
| 20 | 26.8 |
| 21 | 27.4 |
| 23 | 6.4 |
| 24 | 8.4 |
| 25 | 6.7 |
| 26 | 36.2 |
| 27 | 15.7 |
| 28 | 6.8 |
| 29 | 12.5 |
| 30 | 5.9 |
| 31 | 20.4 |
| 32 | 6.5 |
| 33 | 33.0 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Preparation of the compounds of present invention:

Compounds of formula I can be prepared as shown in the following description:

Route 1 is Described in Example 1

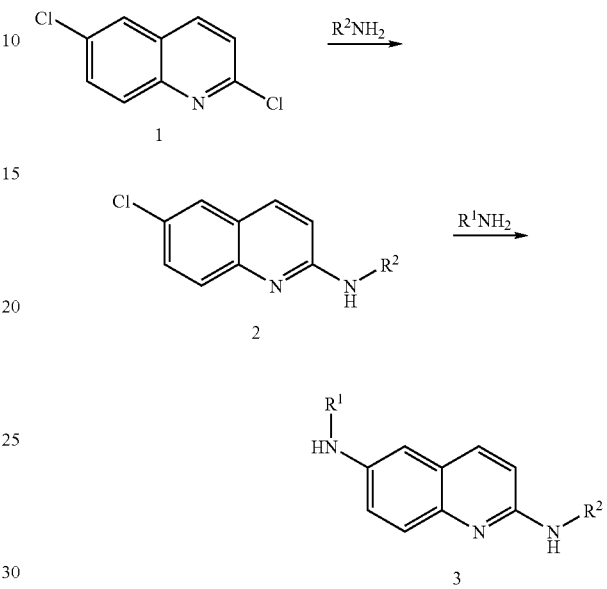

2,6-Dichloro-quinoline (1) is reacted with 2 equivalents of an amine ($R^2NH_2$) without solvent. Intermediate (2) is reacted with a second amine ($R^1NH_2$) in a palladium catalyzed substitution reaction to produce 3, wherein $R^1$ is alkyl, haloalkyl, cyanoalkyl, hydroxyalkyl, -alkylene-cycloalkyl, -alkylene-heterocycloalkyl, -alkylene-$NR^eR^f$, -alkylene-O-alkyl, or -alkylene-$S(O)_x$-alkyl; preferably $R^1$ is alkyl, -alkylene-cycloalkyl, -alkylene-heterocycloalkyl, -alkylene-$NR^eR^f$, or -alkylene-O-alkyl.

Route 2 is Described in Example 10

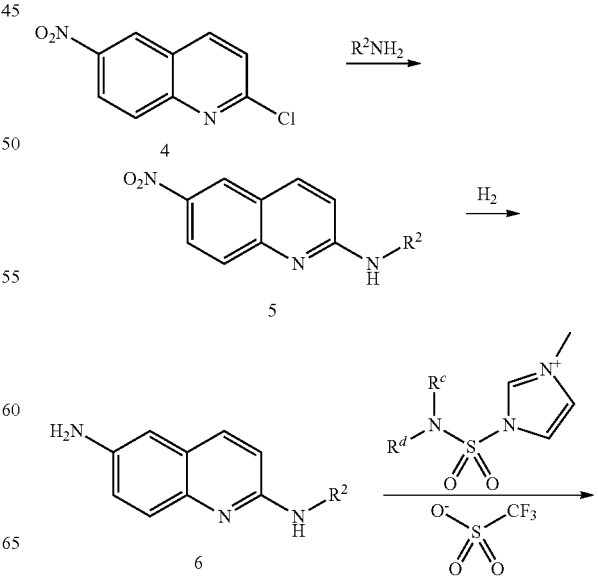

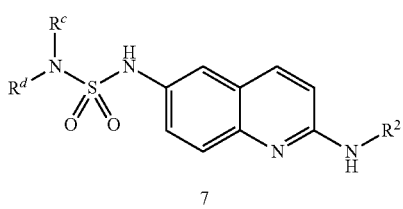

2-Chloro-6-nitro-quinoline (4) is reacted with 2 equivalents of an amine ($R^2NH_2$) without solvent. Intermediate (5) is reduced with hydrogen to the amine 6 which is reacted with a trifluoro-methanesulfonate 3-sulfamoyl-1-methyl-3-H-imidazol-1-ium salt to the sulfamide 7. $R^c$ and $R^d$ are each independently H, alkyl, cycloalkyl, or heterocycloalkyl, preferably from H, alkyl or cycloalkyl.

Route 3 is Described in Example 14

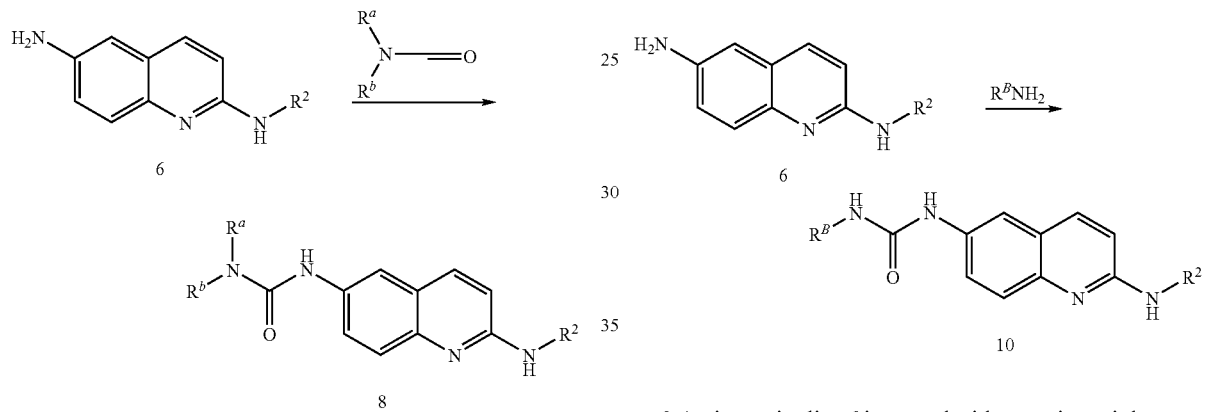

Intermediate 6 is reacted with an isocyanate to the urea 8. $R^a$ and $R^b$ are each independently H, alkyl cycloalkyl, or heterocycloalkyl; preferably H, alkyl, or heterocycloalkyl.

Route 4 is Described in Example 16

6-Amino-quinoline 6 is treated with an acid in the presence of 2-(1H-benzotriazole-1-yl)-1,1,3,3-tetramethyluronium tetrafluoroborate (HOBt) and N,N-diisopropyl ethyl amine with or without 1-(3-dimethylaminopropyl)-3-ethylcarbodiimide hydrochloride (EDC) to yield carboxamide derivative 9. $R^A$ is cycloalkyl, alkyl, alkylene-cycloalkyl, -alkylene-heterocycloalkyl, heterocycloalkyl, or $-NR^aR^b$, wherein $R^a$ and $R^b$ are each independently H, alkyl, cycloalkyl, or heterocycloalkyl; preferably H, alkyl, or heterocycloalkyl. Hence, $R^1$ is $-C(O)$-cycloalkyl, $-C(O)$-alkyl, $-C(O)$-alkylene-cycloalkyl, $-C(O)$-alkylene-heterocycloalkyl, $-C(O)$-heterocycloalkyl, or $-C(O)-NR^aR^b$, wherein $R^a$ and $R^b$ are each independently H, alkyl, cycloalkyl, or heterocycloalkyl; preferably H, alkyl, or heterocycloalkyl.

The following coupling reagents can be chosen alternatively: a mixture of N-ethyldiisopropylamine and O-(benzotriazol-1-yl)-N,N,N',N'-tetramethyluronium-tetrafluoroborate (TBTU). Alternatives include O-(benzotriazol-1-yl)-N,N,N',N'-tetramethyluronium-hexafluoroborate (HBTU), benzotriazol-1-yloxy)-tris-(dimethylamino)-phosphonium-hexafluorophosphate (BOP), benzotriazol-1-yloxy)-tripyrrolidinophosphonium-hexafluorophosphate (PyBOP), and O-(benzotriazol-1-yl)-N,N,N',N'-bis-(tetramethylen)-uronium-hexafluorophosphate (HBPyU).

Route 5 Described in Example 17

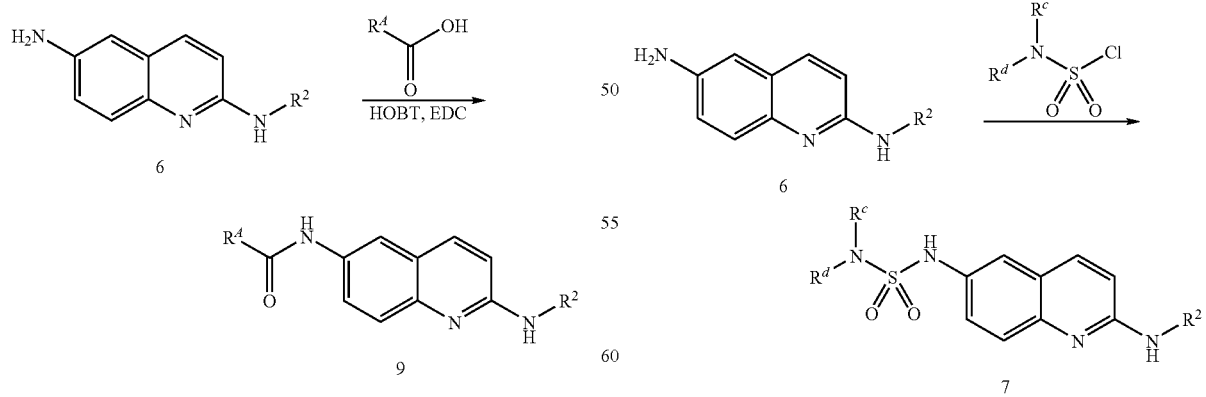

6-Amino-quinoline 6 is treated with an amine, triphosgene and triethylamine in tetrahydrufuran to yield urea derivative 10. $R^B$ is alkyl, cycloalkyl, or heterocycloalkyl. Hence, $R^1$ is selected from $-C(O)NR^aR^b$ wherein $R^a$ is H and $R^b$ is alkyl, cycloalkyl, or heterocycloalkyl.

Route 6 is Described in Example 20

6-Amino-quinoline 6 is reacted with a sulfamoyl chloride in pyridine to the sulfamide 7. $R^c$ and $R^d$ are each independently H, alkyl, cycloalkyl, or heterocycloalkyl, preferably from H, alkyl or cycloalkyl. Hence, $R^1$ is $-S(O)_2NR^cR^d$.

Route 7 is Described in Example 32

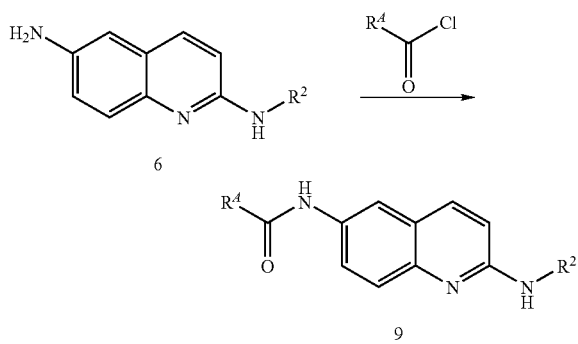

6-Amino-quinoline 6 is reacted with an acid chloride to the amide 9. $R^A$ is cycloalkyl, alkyl, alkylene-cycloalkyl, -alkylene-heterocycloalkyl, heterocycloalkyl, or —$NR^aR^b$, wherein $R^a$ and $R^b$ are each independently H, alkyl, cycloalkyl, or heterocycloalkyl; preferably H, alkyl, or heterocycloalkyl. Hence, $R^1$ is —C(O)-cycloalkyl, —C(O)-alkyl, —C(O)-alkylene-cycloalkyl, —C(O)-alkylene-heterocycloalkyl, —C(O)heterocycloalkyl, or —C(O)—$NR^aR^b$, wherein $R^a$ and $R^b$ are each independently H, alkyl, cycloalkyl, or heterocycloalkyl; preferably H, alkyl, or heterocycloalkyl.

EXAMPLES

Example 1

$N^6$-(2-Dimethylamino-ethyl)-$N^2$-(2-phenoxy-ethyl) quinoline-2,6-diamine

Step A: A stirred mixture of 2,6-dichloro-quinoline (1.0 g, 5.1 mmol) and 2-phenoxyethylamine (1.5 g, 11 mmol) was heated in the microwave for 1 h at 120° C. Purification by flash chromatography on silica gel (ethyl acetate/heptane 100:0→70:30) yielded (6-chloro-quinolin-2-yl)-(2-phenoxy-ethyl)-amine as a light yellow oil (1.1 g, 73%), MS: m/e=299.3 (M+H$^+$).

Step B: (6-Chloro-quinolin-2-yl)-(2-phenoxy-ethyl)-amine (100 mg, 0.33 mmol) was dissolved in 1.5 mL dioxane. Argon was bubbled through the solution for 2 minutes to remove oxygen. N,N-Dimethylethylendiamine (149 mg, 1.69 mmol), sodium tert.-butylate (80 mg, 0.83 mmol), 1,1'-bis(diphenylphosphin)ferrocen (21 mg, 0.037 mmol) and 1,1'-bis(diphenyl-phosphin)ferrocen-palladium(II)chloride (10 mg, 0.012 mmol) were added. The reaction mixture was stirred in a sealed tube at 120° C. overnight. The solvent was evaporated and the residue purified by flash chromatography on silica gel (dichloromethane/methanol 100:0→90:10 gradient). The title compound was obtained as a brown oil (35 mg, 30%), MS: m/e=351.3 (M+H$^+$).

Example 2

$N^6$-(3-Dimethylamino-propyl)-$N^2$-(2-phenoxy-ethyl)-quinoline-2,6-diamine

The title compound, MS: m/e=365.1 (M+H$^+$), was prepared in accordance with the general method of example 1 from 2,6-dichloroquinoline, 2-phenoxyethylamine and 3-dimethylamino-propylamine.

Example 3

$N^6$-Ethyl-$N^2$-(2-phenoxy-ethyl)-quinoline-2,6-diamine

The title compound, MS: m/e=308.4 (M+H$^+$), was prepared in accordance with the general method of example 1 from 2,6-dichloroquinoline, 2-phenoxyethylamine and ethylamine (solution in tetrahydrofurane).

Example 4

$N^2$-(2-Methoxy-benzyl)-$N^6$-(2-morpholin-4-yl-ethyl)-quinoline-2,6-diamine

The title compound, MS: m/e=393.4 (M+H$^+$), was prepared in accordance with the general method of example 1 from 2,6-dichloroquinoline, 2-methoxybenzylamine and N-(2-aminoethyl)morpholine.

Example 5

$N^2$-(2-Methoxy-benzyl)-$N^6$-(3-morpholin-4-yl-propyl)-quinoline-2,6-diamine

The title compound, MS: m/e=407.5 (M+H$^+$), was prepared in accordance with the general method of example 1 from 2,6-dichloroquinoline, 2-methoxybenzylamine and 4-(3-aminopropyl)morpholine.

Example 6

$N^6$-(2-Methoxy-ethyl)-$N^2$-(5-methyl-furan-2-ylmethyl)-quinoline-2,6-diamine

The title compound, MS: m/e=312.1 (M+H$^+$), was prepared in accordance with the general method of example 1 from 2,6-dichloroquinoline, 5-methyl-2-furanmethanamine and 2-methoxyethylamine.

Example 7

$N^6$-(3-Methoxy-propyl)-$N^2$-(5-methyl-furan-2-ylmethyl)-quinoline-2,6-diamine The title compound, MS: m/e=326.1 (M+H$^+$), was prepared in accordance with the general method of example 1 from 2,6-dichloroquinoline, 5-methyl-2-furanmethanamine and 3-methoxypropylamine.

Example 8

$N^6$-Cyclopropylmethyl-$N^2$-(5-methyl-furan-2-ylmethyl)-quinoline-2,6-diamine

The title compound, MS: m/e=308.4 (M+H$^+$), was prepared in accordance with the general method of example 1 from 2,6-dichloroquinoline, 5-methyl-2-furanmethanamine and aminomethylcyclopropane.

Example 9

$N^6$-Cyclohexyl-$N^2$-(5-methyl-furan-2-ylmethyl)-quinoline-2,6-diamine

The title compound, MS: m/e=336.5 (M+H$^+$), was prepared in accordance with the general method of example 1 from 2,6-dichloroquinoline, 5-methyl-2-furanmethanamine and cyclohexylamine.

Example 10

N'-{2-[(2-methoxybenzyl)amino]quinolin-6-yl}-N, N-dimethylsulfamide

Step A: 2-Chloro-6-nitro-quinoline (0.80 g, 4.0 mmol) and 2-methoxybenzylamine (1.5 mL, 12 mmol) were heated at 130° C. for 2 h. The reaction mixture was purified by flash chromatography on silica gel (heptane/ethyl acetate, 9:1, 4:1, 1:1). (2-Methoxy-benzyl)-(6-nitro-quinolin-2-yl)-amine was obtained as a yellow solid (0.5 g, 42%), MS: m/e=310.5 (M+H$^+$).

Step B: (2-Methoxy-benzyl)-(6-nitro-quinolin-2-yl)-amine (0.5 g, 2.0 mmol) were dissolved in ethyl acetate (25 ml). Upon addition of Pd/C (10%, 0.1 g) the reaction mixture was stirred for 45 min at ambient temperature under an atmosphere of hydrogen. Then the catalyst was filtered off, the filter washed with ethyl acetate and the filtrate evaporated. $N^2$-(2-Methoxy-benzyl)-quinoline-2,6-diamine was obtained as a yellow foam (0.40 g, 87%); MS: m/e=280.5 (M+H$^+$).

Step C: $N^2$-(2-Methoxy-benzyl)-quinoline-2,6-diamine (70 mg, 0.251 mmol) was dissolved in 2 mL acetonitrile. Trifluoro-methanesulfonate3-dimethylsulfamoyl-1-methyl-3-H-imidazol-1-ium (102 mg, 0.339 mmol) was added and the reaction mixture was stirred at 80° C. overnight. The solvent was evaporated off and the residue purified by flash chromatography on silica gel (heptane/ethyl acetate 80:20→34:66 gradient). The title compound was obtained as a yellow foam (55 mg, 56%), MS: m/e=387.1 (M+H$^+$).

Example 11

N,N-Dimethyl-N'-(2-{[(5-methyl-2-furyl)methyl]amino}quinolin-6-yl)sulfamide

The title compound, MS: m/e=361.0 (M+H$^+$), was prepared in accordance with the general method of example 10 from 2-chloro-6-nitro-quinoline, 5-methyl-2-furanmethanamine and trifluoro-methanesulfonate3-dimethylsulfamoyl-1-methyl-3-H-imidazol-1-ium.

Example 12

N,N-dimethyl-N'-{2-[(2-methyl-2,3-dihydro-benzofuran-7-yl)amino]quinolin-6-yl}sulfamide The title compound, MS: m/e=399.3 (M+H$^+$), was prepared in accordance with the general method of example 10 from 2-chloro-6-nitro-quinoline, 2,3-dihydro-2-methyl-7-benzofuranamine (CAS 26210-74-2) and trifluoro-methanesulfonate3-dimethylsulfamoyl-1-methyl-3-H-imidazol-1-ium.

Example 13

N'-{2-[(2,2-dimethyl-2,3-dihydro-benzofuran-7-yl)amino]quinolin-6-yl}-N,N-dimethylsulfamide The title compound, MS: m/e=413.4 (M+H$^+$), was prepared in accordance with the general method of example 10 from 2-chloro-6-nitro-quinoline, 7-amino-2,3-dihydro-2,2-dimethylbenzofuran (CAS 68298-46-4) and trifluoro-methanesulfonate3-dimethylsulfamoyl-1-methyl-3-H-imidazol-1-ium.

Example 14

1-Isopropyl-3-[2-(2-methoxy-benzylamino)-quinolin-6-yl]-urea $N^2$-(2-Methoxy-benzyl)-quinoline-2,6-diamine (example 10, step B, 50 mg, 0.179 mmol) was dissolved in 1 mL toluene. Isopropyl isocyanate (15 mg, 0.179 mmol) was added and the reaction mixture was stirred at 60° C. overnight. The reaction mixture was cooled to room temperature and the crystals were filtered off and washed with dichloromethane. The title compound was obtained as an off-white solid (24 mg, 37%), MS: m/e=365.3 (M+H$^+$).

Example 15

1-Isopropyl-3-[2-(2-methyl-2,3-dihydro-benzofuran-7-ylamino)quinolin-6-yl]-urea

The title compound, MS: m/e=377.4 (M+H$^+$), was prepared in accordance with the general method of example 14 from 2-chloro-6-nitro-quinoline, 2,3-dihydro-2-methyl-7-benzofuranamine (CAS 26210-74-2) and isopropyl isocyanate.

Example 16

1-Methyl-piperidine-4-carboxylic acid [2-(2-methoxy-benzylamino)-quinolin-6-yl]-amide To a stirred solution of 1-methyl-piperidine-4-carboxylic acid hydrochloride salt (35 mg, 179 mmol) in tetrahydrofurane (3 ml) were added at room temperature N-ethyldiisopropylamine (74 mg, 0.573 mmol), 2-(1H-benzotriazole-1-yl)-1,1,3,3-tetramethyluronium tetrafluoroborate (27 mg, 0.197 mmol), N,N-diisopropyl ethyl amine (74 mg, 0.197 mmol) and 1-(3-dimethylamino-propyl)-3-ethylcarbodiimide hydrochloride (38 mg, 0.197 mmol) and the mixture was allowed to stir for 90 min. $N^2$-(2-Methoxy-benzyl)-quinoline-2,6-diamine (example 10, step B, 50 mg, 0.179 mmol) was added and the reaction mixture was allowed to stir for 17 h, poured into sat. sodium bicarbonate solution (30 ml) and extracted with dichloromethane (2×30 ml). The combined organic layers were washed with water (30 ml), dried (MgSO4) and evaporated. The crude product was further purified by flash chromatography on silica gel (heptane/ethyl acetate) and crystallization (ethyl acetate/heptane) to yield the title compound as white solid (35 mg, 48%). MS: m/e=405.5 (M+H$^+$).

Example 17

1-[2-(2-Methoxy-benzylamino)-quinolin-6-yl]-3-(1-methyl-piperidin-4-yl)-urea $N^2$-(2-Methoxy-benzyl)-quinoline-2,6-diamine (example 10, step B, 65 mg, 0.233 mmol) was dissolved in tetrahydrofuran (3 ml) and triethylamine (0.052 mL, 0.512 mmol) was added. At 0° C. bis(trichloromethyl)carbonate (31 mg, 0.105 mmol) was added and the reaction mixture subsequently heated to 80° C. for 3 h. Upon cooling to ambient temperature triethylamine (0.052 mL, 0.512 mmol) and 1-methyl-piperidin-4-ylamine (27 mg, 0.233 mmol) were added and the whole reaction mixture was stirred over night at 50° C. After evaporation of the solvent, the residue was taken up in water and extracted with ethyl acetate. The combined organic phases were dried on sodium sulfate, filtered and the filtrate was evaporated. The crude product was purified by flash chromatography on silica gel (dichloromethane/methanol) and to yield the title compound as white solid (15 mg, 15%). MS: m/e=420.4 (M+H$^+$).

Example 18

1-Isopropyl-3-[2-(4-methoxy-benzylamino)-quinolin-6-yl]-urea

The title compound, MS: m/e=365.1 (M+H$^+$), was prepared in accordance with the general method of example 14 from 2-chloro-6-nitro-quinoline, 4-methoxy-benzylamine and isopropyl isocyanate.

Example 19

(1S,4S)-2-Oxa-5-aza-bicyclo[2.2.1]heptane-5-sulfonic acid [2-(2-methoxy-benzylamino)-quinolin-6-yl]-amide The title compound, MS: m/e=441.3 (M+H$^+$), was prepared in accordance with the general method of example 10 from 2-chloro-6-nitro-quinoline, 2-methoxy-benzylamine and trifluoro-methanesulfonate1-methyl-3-[(1S,4S)-(2-oxa-5-aza-bicyclo[2.2.1]hept-5-yl)sulfonyl]-3H-imidazol-1-ium.

Example 20

N-cyclopropyl-N'-{2-[(2-methoxybenzyl)amino]quinolin-6-yl}sulfamide

N$^2$-(2-Methoxy-benzyl)-quinoline-2,6-diamine (example 10, step B, 40 mg, 0.143 mmol) was dissolved in 1 mL pyridine. Cyclopropylsulfamoyl chloride (29 mg, 0.186 mmol) was added and the reaction mixture was stirred at room temperature overnight. The solvent was evaporated off and the residue purified by flash chromatography on silica gel (heptane/ethyl acetate 90:10→34:66 gradient). The title compound was obtained as a yellow solid (22 mg, 39%), MS: m/e=397.5 (M+H$^+$).

Example 21

1-Isopropyl-3-{2-[(5-methyl-furan-2-ylmethyl)-amino]-quinolin-6-yl}-urea

The title compound, MS: m/e=339.3 (M+H$^+$), was prepared in accordance with the general method of example 14 from 2-chloro-6-nitro-quinoline, 5-methyl-2-furanmethanamine and isopropyl isocyanate.

Example 22

1-[2-(2,4-Dimethoxy-benzylamino)-quinolin-6-yl]-3-isopropyl-urea

The title compound, MS: m/e=395.4 (M+H$^+$), was prepared in accordance with the general method of example 14 from 2-chloro-6-nitro-quinoline, 2,4-dimethoxy-benzylamine and isopropyl isocyanate.

Example 23

1-[2-(2-Methoxy-benzylamino)-quinolin-6-yl]-3-[1-(2-methoxy-ethyl)-piperidin-4-yl]-urea The title compound, MS: m/e=464.4 (M+H$^+$), was prepared in accordance with the general method of example 17 from 2-chloro-6-nitro-quinoline, 2-methoxy-benzylamine and 1-(2-methoxyethyl)piperidine-4-amine (CAS 502639-08-9).

Example 24

1-[1-(2-Fluoro-ethyl)-piperidin-4-yl]-3-[2-(2-methoxy-benzylamino)-quinolin-6-yl]-urea The title compound, MS: m/e=452.4 (M+H$^+$), was prepared in accordance with the general method of example 17 from 2-chloro-6-nitro-quinoline, 2-methoxy-benzylamine and 1-(2-fluoroethyl)piperidine-4-amine (CAS 947263-70-9).

Example 25

1-(1-Isopropyl-piperidin-4-yl)-3-[2-(2-methoxy-benzylamino)-quinolin-6-yl]-urea

The title compound, MS: m/e=448.3 (M+H$^+$), was prepared in accordance with the general method of example 17 from 2-chloro-6-nitro-quinoline, 2-methoxy-benzylamine and (1-isopropylpiperidine-4-yl)amine (CAS 127285-08-9).

Example 26

1-[2-2-Methoxy-benzylamino)-quinolin-6-yl]-3-[1-(3,3,3-trifluoro-propionyl)-piperidin-4-yl]-urea The title compound, MS: m/e=516.0 (M+H$^+$), was prepared in accordance with the general method of example 17 from 2-chloro-6-nitro-quinoline, 2-methoxy-benzylamine and 1-(4-amino-1-piperidinyl)-3,3,3-trifluoro-1-propanone (CAS 926240-87-1).

Example 27

1-[1-(2-Fluoro-acetyl)-piperidin-4-yl]-3-[2-(2-methoxy-benzylamino)-quinolin-6-yl]-urea The title compound, MS: m/e=466.3 (M+H$^+$), was prepared in accordance with the general method of example 17 from 2-chloro-6-nitro-quinoline, 2-methoxy-benzylamine and 1-(fluoroacetyl)-4-piperidinamine (CAS 791061-33-1).

Example 28

1-(1-Cyclopropyl-piperidin-4-yl)-3-[2-(2-methoxy-benzylamino)-quinolin-6-yl]-urea The title compound, MS: m/e=446.3 (M+H$^+$), was prepared in accordance with the general method of example 17 from 2-chloro-6-nitro-quinoline, 2-methoxy-benzylamine and 1-(cyclopropylpiperidin-4-yl)amine (CAS 62813-02-9).

Example 29

1-{2-[(5-Methyl-furan-2-ylmethyl)-amino]-quinolin-6-yl}-3-(1-methyl-piperidin-4-yl)-urea The title compound, MS: m/e=394.4 (M+H$^+$), was prepared in accordance with the general method of example 17 from 2-chloro-6-nitro-quinoline, 5-methyl-2-furanmethanamine and 1-(methylpiperidin-4-yl)amine.

Example 30

1-[2-(2-Methoxy-benzylamino)-quinolin-6-yl]-3-[1-(2-methylsulfanyl-ethyl)-piperidin-4-yl]-urea The title compound, MS: m/e=480.4 (M+H⁺), was prepared in accordance with the general method of example 17 from 2-chloro-6-nitro-quinoline, 2-methoxy-benzylamine and 1-(cyclopropylpiperidin-4-yl)amine (CAS 62813-02-9).

Example 31

1-[1-(2-Methoxy-acetyl)-piperidin-4-yl]-3-[2-(2-methoxy-benzylamino)-quinolin-6-yl]-urea The title compound, MS: m/e=478.1 (M+H⁺), was prepared in accordance with the general method of example 17 from 2-chloro-6-nitro-quinoline, 2-methoxy-benzylamine and 1-(4-amino-1-piperidinyl)-2-methoxy-ethanone (CAS 926260-72-2).

Example 32

Cyclopropanecarboxylic acid [2-(2-methoxy-benzylamino)-quinolin-6-yl]-amide

N²-(2-Methoxy-benzyl)-quinoline-2,6-diamine (example 10, step B, 150 mg, 0.537 mmol) was dissolved in 6 mL acetonitrile and 6 mL saturated sodium bicarbonate solution. Cyclopropane carbonyl chloride (63 mg, 0.60 mmol) was added and the reaction mixture was stirred at room temperature overnight. The reaction mixture was diluted with 50 mL water and extracted with ethyl acetate (3×50 ml). The combined organic layers were washed with water (30 ml), dried with sodium sulfate and evaporated. The crude product was recrystallized from diisopropyl ether. The title compound was obtained as a white solid (123 mg, 66%), MS: m/e=348.3 (M+H⁺).

Example 32

N-[2-(2-Methoxy-benzylamino)-quinolin-6-yl]-2-(4-methyl-piperazin-1-yl)-acetamide The title compound, MS: m/e=420.0 (M+H⁺), was prepared in accordance with the general method of example 16 from 2-chloro-6-nitro-quinoline, 2-methoxy-benzylamine and 4-methyl-piperazin-1-yl acetic acid.

The invention claimed is:

1. A compound of formula (I)

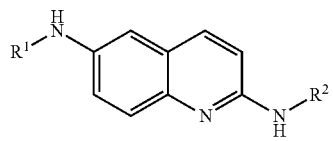

I wherein
R¹ is —C(O)-cycloalkyl, —C(O)-alkyl, —C(O)-alkylene-cycloalkyl, —C(O)-alkylene-heterocycloalkyl, —C(O)-heterocycloalkyl, —C(O)—NRᵃRᵇ, —S(O)₂-heterocycloalkyl, —S(O)₂—NRᶜRᵈ, alkyl, haloalkyl, cyanoalkyl, hydroxyalkyl, -alkylene-cycloalkyl, -alkylene-heterocycloalkyl, -alkylene-NRᵉRᶠ, -alkylene-O-alkyl, or -alkylene-S(O)ₓ-alkyl;
x is 0, 1 or 2;
Rᵃ, Rᵇ, Rᶜ, Rᵈ, Rᵉ, and Rᶠ are each independently selected from H, alkyl, cycloalkyl, and heterocycloalkyl;
heterocycloalkyl is unsubstituted or substituted with one or more substituents independently selected from alkyl, hydroxy, hydroxyalkyl, benzyl, oxo, —C(O)Oalkyl, cycloalkyl, alkylene-O-alkyl, —C(O)haloalkyl, —C(O)-alkylene-O-alkyl, cyanoalkyl, alkylene-S(O)ₓ-alkyl, -alkylene-C(O)N(alkyl)₂, halo, haloalkyl and alkoxy;
R² is —Ar¹, —CH₂—Ar¹, or —CH₂CH₂O—Ar¹;
Ar¹ is phenyl or 5- or 6-membered heteroaryl, each unsubstituted or substituted with one or more alkyl, cycloalkyl, alkoxy, haloalkoxy, haloalkyl, halo, OH, or CN, or with two substituents in the ortho-position that form a bridge anellated to the aromatic ring, wherein the bridge is selected from —O—CH₂CH₂O—, —OCHCH₃CH₂—, or —OC(CH₃)₂CH₂—, and wherein phenyl is not substituted with halo in para-position;
or a pharmaceutically acceptable salt thereof.

2. The compound of claim 1, wherein
R¹ is —C(O)-cycloalkyl, —C(O)-alkylene-heterocycloalkyl, —C(O)-heterocycloalkyl, —C(O)—NRᵃRᵇ, —S(O)₂-heterocycloalkyl, —S(O)₂—NRᶜRᵈ, alkyl, -alkylene-cycloalkyl, -alkylene-heterocycloalkyl, -alkylene-NRᵉRᶠ, or -alkylene-O-alkyl,
Rᵃ, Rᵇ, Rᶜ, Rᵈ, Rᵉ, and Rᶠ are each independently selected from H, alkyl, cycloalkyl, and heterocycloalkyl; and
heterocycloalkyl is unsubstituted or substituted with one or more substituents independently selected from alkyl, —C(O)haloalkyl, —C(O)-alkylene-O-alkyl, alkylene-S(O)ₓ-alkyl, and haloalkyl; and
x is 0, 1 or 2.

3. The compound of claim 1, wherein
Rᵃ and Rᵇ are each independently selected from H, alkyl, and heterocycloalkyl.

4. The compound of claim 1, wherein
Rᶜ and Rᵈ are each independently selected from H, alkyl and cycloalkyl.

5. The compound of claim 1, wherein
Rᵉ and Rᶠ are alkyl.

6. The compound of claim 1, wherein
heterocycloalkyl is morpholinyl, piperidinyl, piperazinyl or 2-oxa-5-aza-hicyclo[2.2.1]heptyl, each unsubstituted or substituted with one or more substituents independently selected from alkyl, —C(O)haloalkyl, —C(O)-alkylene-O-alkyl, alkylene-S(O)ₓ-alkyl, and haloalkyl.

7. The compound of claim 1, wherein
R² is —Ar¹, —CH₂—Ar¹, or —CH₂CH₂O—Ar¹; wherein
Ar¹ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—CH₂CH₂O—, —OCHCH₃CH₂—, and —OC(CH₃)₂CH₂—.

8. The compound of claim 1, wherein
R² is —Ar¹, wherein
Ar¹ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—CH₂CH₂O—, —OCHCH₃CH₂—, and —OC(CH₃)₂CH₂—.

9. The compound of claim 1, wherein $R^2$ is —$CH_2$—$Ar^1$, wherein $Ar^1$ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—$CH_2CH_2O$—, —$OCHCH_3CH_2$—, and —$OC(CH_3)_2CH_2$—.

10. The compound of claim 1, wherein $R^2$ is —$CH_2CH_2O$—$Ar^1$; wherein $Ar^1$ is phenyl or 5- or 6-membered heteroaryl, each unsubstituted or substituted with one or more alkyl, cycloalkyl, alkoxy, haloalkoxy, haloalkyl, OH, or CN, or with two substituents in the ortho-position that form a bridge anellated to the aromatic ring, wherein the bridge is selected from —O—$CH_2CH_2O$—, —$OCHCH_3CH_2$—, and —$OC(CH_3)_2CH_2$—.

11. The compound of claim 1, wherein $R^2$ is —$Ar^1$, —$CH_2$—$Ar^1$, or —$CH_2CH_2O$—$Ar^1$; wherein $Ar^1$ is phenyl or 5- or 6-membered heteroaryl, each unsubstituted or substituted with one or more alkyl or alkoxy, or with two substituents in the ortho-position and that form a bridge anellated to the aromatic ring, the bridge being selected from —$OCHCH_3CH_2$— and —$OC(CH_3)_2CH_2$—.

12. The compound of claim 1, wherein heteroaryl is furanyl.

13. The compound of claim 1, wherein $R^2$ is —$Ar^1$, —$CH_2$—$Ar^1$, or —$CH_2CH_2O$—$Ar^1$; wherein $Ar^1$ is phenyl, 4-methoxy-phenyl, 2-methoxy-phenyl, 2,4-dimethoxy-phenyl, 5-methyl-furan-2-yl, 2-methyl-2,3-dihydro-benzofuran-7-yl, or 2,2-dimethyl-2,3-dihydro-benzofuran-7-yl.

14. A pharmaceutical composition comprising a therapeutically effective amount of a compound of formula I

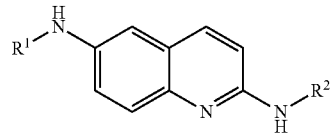

wherein $R^1$ is —C(O)-cycloalkyl, —C(O)-alkyl, —C(O)-alkylene-cycloalkyl, —C(O)-alkylene-heterocycloalkyl, —C(O)-heterocycloalkyl, —C(O)—$NR^aR^b$, —$S(O)_2$-heterocycloalkyl, —$S(O)_2$—$NR^cR^d$, alkyl, haloalkyl, cyanoalkyl, hydroxyalkyl, -alkylene-cycloalkyl, -alkylene-heterocycloalkyl, -alkylene-$NR^eR^f$, -alkylene-O-alkyl, or -alkylene-$S(O)_x$-alkyl;

x is 0, 1 or 2;

$R^a$, $R^b$, $R^c$, $R^d$, $R^e$, and $R^f$ are each independently selected from H, alkyl, cycloalkyl, and heterocycloalkyl;

heterocycloalkyl is unsubstituted or substituted with one or more substituents independently selected from alkyl, hydroxy, hydroxyalkyl, benzyl, oxo, —C(O)Oalkyl, cycloalkyl, alkylene-O-alkyl, —C(O)haloalkyl, —C(O)-alkylene-O-alkyl, cyanoalkyl, alkylene-$S(O)_x$-alkyl, -alkylene-C(O)N(alkyl)$_2$, halo, haloalkyl and alkoxy;

$R^2$ is —$Ar^1$, —$CH_2$—$Ar^1$, or —$CH_2CH_2O$—$Ar^1$;

$Ar^1$ is phenyl or 5- or 6-membered heteroaryl, each unsubstituted or substituted with one or more alkyl, cycloalkyl, alkoxy, haloalkoxy, haloalkyl, halo, OH, or CN, or with two substituents in the ortho-position that form a bridge anellated to the aromatic ring, wherein the bridge is selected from —O—$CH_2CH_2O$—, —$OCHCH_3CH_2$—, or —$OC(CH_3)_2CH_2$—, and wherein phenyl is not substituted with halo in para-position;

or a pharmaceutically acceptable salt thereof and a pharmaceutically acceptable carrier.

* * * * *